United States Patent [19]
Shintaku

[11] Patent Number: 5,710,364
[45] Date of Patent: Jan. 20, 1998

[54] CRUCIFEROUS PLANT HAVING A HIGH CAROTENE CONTENT

[76] Inventor: Yurie Shintaku, 10-2, Shimizu 2-chome, Suginami-ku, Tokyo, Japan

[21] Appl. No.: 359,061

[22] Filed: Dec. 19, 1994

[30] Foreign Application Priority Data

Dec. 24, 1993 [JP] Japan .................................. 5-326913

[51] Int. Cl.$^6$ .............................. A01H 5/00; A01H 1/00
[52] U.S. Cl. ............ 800/200; 800/255; 800/DIG. 15; 800/DIG. 16; 47/58; 47/DIG. 1
[58] Field of Search .................................. 800/200, 255, 800/DIG. 15, DIG. 16; 47/58, DIG. 1

[56] References Cited

PUBLICATIONS

Dickson, et al., "Orange–curd High Carotene Cauliflower Inbreds NY 156, NY 163 and NY 165'", Aug. 1988, HortScience, vol. 23, No. 4, pp. 778–779.

Hoser–Krauze, et al., "Orange Curd High Carotene Cauliflower F1 Hybrids'", Mar. 1994, Cruciferae Newsletter, vol. 16, pp. 137–138.

Gross, "The pigments of 3 hybrid varieties of broccoli *Brassica olaracea*—var. *italica*'", 1979, Gartenbauwissenschaft, vol. 44, No. 5, pp. 213–216.

Ockendon, "Rare self incompatibility alleles in a purple cultivar of brussels–sprouts", 1977, Heredity, vol. 39, No. 1, pp. 149–152.

Baggett, "Inheritance of internal pigmentation in green cabbage *Brassica–olaracea* var. *capitata*", 1978, Euphytica, vol. 27, No. 2, pp. 593–599.

*Primary Examiner*—Douglas W. Robinson
*Assistant Examiner*—Melissa L. Kimball
*Attorney, Agent, or Firm*—David F. Kleinsmith; Gray Cary Ware & Freidenrich

[57] ABSTRACT

There is provided a novel cruciferous plant having an or gene and containing a large quantity of carotene even in those parts where a conventional cruciferous plant contains little carotene. The cruciferous plant of the present invention is useful as an edible plant or an ornamental plant.

10 Claims, No Drawings

CRUCIFEROUS PLANT HAVING A HIGH CAROTENE CONTENT

This application claims the benefit of Japanese Application No. 326913/1993, filed Dec. 24, 1993, now pending, the entire contents of which are hereby incorporated by reference herein.

BACKGROUND OF THE INVENTION

1. Field of the Invention

The present invention relates to a novel plant belonging to the family Cruciferae and having a high carotene content. More particularly, the present invention is concerned with a cruciferous plant which contains a large quantity of carotene even in those parts where a conventional cruciferous plant contains little carotene.

2. Discussion of Related Art

There are a number of useful plants in the family Cruciferae. Among all, the following four species are especially useful: *Brassica oleracea* L. including cabbage, cauliflower, etc., *Brassica napus* L. including rape, hakuran (a hybrid between cabbage and Chinese cabbage), etc., *Brassica campestris* L. including Chinese cabbage, turnip, etc., and *Raphanus sativus* L. including Japanese radish, etc.

All of those species mentioned above are known to contain carotene in the plant body. However, carotene-containing parts are generally limited to those dark green parts containing a large quantity of chlorophyll, and therefore the color of carotene is seldom observed from outside. In addition, the parts with a high carotene content are generally not edible.

For example, with respect to cabbage, kohlrabi and Brussels sprouts belonging to *Brassica oleracea*, the carotene contents of green parts are high, but those of non-green parts (such as head-forming leaves inside the head of cabbage and Brussels sprouts, and the inside of a kohlrabi corm) are almost zero or extremely low [according to Standard Tables of Food Composition in Japan (4th rev. version), (A. Kayama ed.), Joshi Eiyoh Daigaku Shuppan-bu, Tokyo, 1991, the carotene content of cabbage (head-forming leaves, fresh) is 18 μg/100 g, and that of kohlrabi (corm, fresh) is 50 μg/100 g.] With respect to hakuran belonging to *Brassica napus*, the carotene content of its green leaves is high, but that of head-forming leaves inside the head is rather low [according to the above Standard Tables, the carotene content of hakuran (head-forming leaves, fresh) is 80 μg/100 g]. Also, seeds of these plants contain little carotene. With respect to Chinese cabbage belonging to *Brassica campestris*, the carotene content of the outer green part in head-forming leaves is high, but most of the head-forming leaves inside the head are light yellow or white and contain little carotene [according to the above Standard Tables, the carotene content of Chinese cabbage (head-forming leaves, fresh) is 13 μg/100 g]. With respect to turnip also belonging to *Brassica campestris*, leaves have a high carotene content, but its root part contains no carotene [according to the above Standard Tables, the carotene contents of turnip are 1,800 μg/100 g (leaves, fresh), and 0 μg/100 g (root, fresh)]. With respect to Japanese radish belonging to *Raphanus sativus*, leaves have a high carotene content, but its root part is white and contains no carotene [according to the above Standard Tables, the carotene contents of Japanese radish are 2,600 μg/100 g (leaves, fresh), and 0 μg/100 g (root, fresh)].

As a cruciferous plant containing a large quantity of carotene in non-green parts, there has been known orange cauliflower belonging to *Brassica orelacea*. Orange cauliflower is a cauliflower whose curd except pithy tissue exhibits orange color. The following is known about this cauliflower [M. H. Dikson et al., *Hort. Science* 23(4):778–779, 1988].

1) The color of orange cauliflower is incompletely dominant, being controlled by one gene (genetic symbol: Or).

2) The homozygous individual (OrOr) produces an orange flower head whose color is darker than that of the heterozygous individual (Oror), but the plant height is dwarf in the former and its curd is 3–4 cm or less in diameter.

3) The heterozygous individual (Oror) produces a curd 15–20 cm in diameter which is almost the same size as that of conventional white cauliflower.

4) The orange color is due to carotene.

Accordingly, if it is possible to introduce the Or gene of orange cauliflower into other cruciferous plants and express the gene therein, plants with a high commercial value can be produced.

However, aside from crossing the orange cauliflower with a species of *Brassica oleracea* to which orange cauliflower belongs, it is extremely difficult to interspecifically hybridize *Brassica oleracea* with *Brassica napus*, *Brassica campestris* or *Raphanus sativus*. In such a case, crossbred seeds are hardly obtainable, and even if obtained, most of the individuals growing therefrom are matroclinal (i.e. having the same morphology as that of the female parent). Even when hybrid seeds are obtained by chance, the individuals growing therefrom are sterile in most cases, and thus the maintaining of subsequent generations by selfing or backcrossing is extremely difficult.

Moreover, the curd of orange cauliflower where orange color is expressed is a mass of tissues composed of closely gathered flower buds at the flower stalk differentiation stage, and this mass of tissues is peculiar to cauliflower. Generally, the expression of a gene relating to a pigment is tissue specific for the most part. If a gene producing a pigment is expressed in a specific tissue, usually the gene is not expressed in other tissues. Therefore, no trials have been made to date to introduce Or gene into a plant belonging to a species other than *Brassica oleracea* or a plant belonging to a genus other than Brassica, or even into a different plant within the species *Brassica oleracea*.

SUMMARY OF THE INVENTION

The object of the present invention is to provide a novel cruciferous plant containing a large quantity of carotene even in those parts where a conventional cruciferous plant contains little carotene, by introducing Or gene into a cruciferous plant other than cauliflower.

The present inventors have made detailed investigations into the above-mentioned Or gene, and found that:

1) This gene can be introduced into an extremely wide range of plants.

2) This gene is a unique gene which is expressed in a wide range of tissues in a plant body.

3) Conditioning genes which promote the expression of Or gene are present in some plants belonging to *Brassica oleracea*. The present invention has been completed based on these findings.

In one aspect of the present invention, there is provided a plant belonging to *Brassica oleracea* L. and having a gene which makes the color of a curd in cauliflower orange and at least one conditioning gene which promotes the expression of the above-mentioned gene.

In another aspect of the present invention, there is provided a plant belonging to *Brassica napus* L., *Brassica campestris* L., or *Raphanus sativus* L. and having a gene which makes the color of a curd in cauliflower orange.

In a further aspect of the present invention, there is provided a cultivar of cabbage (*B. oleracea* L. var. capitata L.), kale (*B. oleracea* L. var. acephala DC.), kohlrabi (*B. oleracea* L. var. gongylodes L.), savoy cabbage (*B. oleracea* L. var. bullta DC.), Brussels sprouts (*B. oleracea* L. var. gemmifera Zenk.), broccoli (*B. oleracea* L. var. italica) or chinese kale (*B. oleracea* L. var. alboglabra Bayl.), having a gene which makes the color of a curd in cauliflower orange.

DETAILED DESCRIPTION OF THE INVENTION

Hereinbelow the present invention will be described in detail.

Examples of the plant of the present invention belonging to *Brassica oleracea* include cabbage (*B. oleracea* L. var. capitata L. ), kale (*B. oleracea* L. var. acephala DC.), kohlrabi (*B. oleracea* L. var. gongylodes L.), savoy cabbage (*B. oleracea* L. var. bullta DC.), Brussels sprouts (*B. oleracea* L. var. gemmifera Zenk. ), cauliflower (*B. oleracea* L. var. botrytis L. ), broccoli (*B. oleracea* L. var. italica) or Chinese kale (*B. oleracea* L. var. alboglabra Bayl. ). However, with respect to cauliflower, a variety having Or gene but not having a conditioning gene which promotes the expression of Or gene is not included in the scope of the present invention.

The plant of the present invention belonging to *Brassica oleracea* has a gene which makes the color of a cauliflower curd orange and, preferably, also has a conditioning gene which promotes the expression of the above-mentioned gene. The gene which makes the color of a cauliflower curd orange is usually called Or gene. This gene is contained in, for example, NY163, NY156 and NY165 lines of orange cauliflower. The conditioning gene which promotes the expression of Or gene is a gene contained in conventional cultivars of cabbage, chinese kale and the like which are artificially grown as commercial products. Examples of those cultivars having such gene include a cabbage cultivar "Meitoku" and a Chinese kale cultivar "Kairan".

Seeds of the plants *Brassica oleracea* L. var. capitata L. cabbage cultivar "Meitoku" (ATCC Designation 209219), *B. oleracea* L. var. botrytis L. cauliflower cultivar NY163 (ATCC Designation 209220), and *B. oleracea* L var. alboglabra Bayl. Chinese kale cultivar "Kairan" (ATCC Designation 209221) have been deposited at the American Type Culture Collection, Rockville, Md., U.S.A. (ATCC) under the terms of the Budapest Treaty on the International Recognition of Deposits of Microorganisms for Purposes of Patent Procedure and the Regulations promulgated under this Treaty. The date of deposit is Aug. 27, 1997, end the respective accession numbers are in parentheses next to the plant name. Samples of the seeds are and will be available to industrial property offices and other persons legally entitled to receive them under the terms of said Treaty and Regulations and otherwise in compliance with the patent laws and regulations of the United States of America and all other nations or international organizations in which this application, or an application claiming priority of this application is filed or in which any patent granted on any such application is granted.

Incidentally, the orange cauliflower NY163 inbred line has been obtained from Department of Horticultural Sciences and Food Science, New York State Experimental Station, Cornell University (Geneva, N.Y. 14456, U.S.A.). It is in the possession of the present applicant, and can be released upon request. Also, the present applicant possesses purebred lines of cabbage cultivar "Meitoku" and Chinese kale cultivar "Kairan", and they can be released upon request.

The characteristics of the plant of the present invention belonging to *Brassica oleracea* reside in that it contains a large quantity of carotene in at least one of those parts where a conventional *Brassica oleracea* contains little carotene, and thereby exhibits orange color, light orange color or the like. Examples of such a part include, for cabbage, head-forming leaves inside the head, the petiole of head-forming leaves, vascular bundle in stem, pithy tissue in stem, root, seeds, etc.; for Chinese kale, vascular bundle in stem, pithy tissue in stem, root, seeds, etc.; for kohlrabi, inside of the corm, vascular bundle in stem, pithy tissue in stem, root, seeds, etc.; for Brussels sprouts, head-forming leaves inside the head, the petiole of head-forming leaves, vascular bundle in stem, pithy tissue in stem, root, seeds, etc.; for kale, vascular bundle in stem, pithy tissue in stem, root, seeds, etc.; for savoy cabbage, head-forming leaves inside the head, the petiole of head-forming leaves, vascular bundle in stem, pithy tissue in stem, root, seeds, etc.; and for broccoli, vascular bundle in stem, pithy tissue in stem, root, seeds, etc.

Approximate carotene contents of these parts are as follows. (In parentheses are values for corresponding parts of a corresponding conventional plant.)

Cabbage:

Head-forming leaves inside the head:
100–5,000 µg/100 g (0–50 µg/100 g)

Petiole of head-forming leaves:
50–5,000 µg/100 g (0–20 µg/100 g)

vascular bundle in stem:
50–5,000 µg/100 g (0–20 µg/100 g)

Pithy tissue in stem:
50–5,000 µg/100 g (0–20 µg/100 g)

Root: 20–1,000 µg/100 g (0–9 µg/100 g)

Seeds: 100–5,000 µg/100 g (0–50 µg/100 g)

Chinese kale:

Vascular bundle in stem:
200–5,000 µg/100 g (0–100 µg/100 g)

Pithy tissue in stem:
200–5,000 µg/100 g (0–100 µg/100 g)

Root: 20–1,000 µg/100 g (0–9 µg/100 g)

Seeds: 100–5,000 µg/100 g (0–50 µg/100 g)

Kohlrabi:

Inside of the corm:
100–5,000 µg/100 g (0–50 µg/100 g)

Vascular bundle in stem:
100–5,000 µg/100 g (0–50 µg/100 g)

Pithy tissue in stem:
100–5,000 µg/100 g (0–50 µg/100 g)

Root: 20–1,000 µg/100 g (0–9 µg/100 g)

Seeds: 100–5,000 µg/100 g (0–50 µg/100 g)

Brussels sprouts:

Head-forming leaves inside the head:
200–5,000 µg/100 g (0–100 µg/100 g)

Petiole of head-forming leaves:
50–5,000 µg/100 g (0–20 µg/100 g)

Vascular bundle in stem:
200–5,000 µg/100 g (0–100 µg/100 g)

Pithy tissue in stem:
  200–5,000 µg/100 g (0–100 µg/100 g)
Root: 20–1,000 µg/100 g (0–9 µg/100 g)
Seeds: 100–5,000 µg/100 g (0–50 µg/100 g)
Kale:
Vascular bundle in stem:
  50–5,000 µg/100 g (0–20 µg/100 g)
Pithy tissue in stem:
  50–5,000 µg/100 g (0–20 µg/100 g)
Root: 20–1,000 µg/100 g (0–9 µg/100 g)
Seeds: 100–5,000 µg/100 g (0–50 µg/100 g)
Savoy cabbage:
Head-forming leaves inside the head:
  100–5,000 µg/100 g (0–50 µg/100 g)
Petiole of head-forming leaves:
  50–5,000 µg/100 g (0–20 µg/100 g)
Vascular bundle in stem:
  50–5,000 µg/100 g (0–20 µg/100 g)
Pithy tissue in stem:
  50–5,000 µg/100 g (0–20 µg/100 g)
Root: 20–1,000 µg/100 g (0–9 µg/100 g)
Seeds: 100–5,000 µg/100 g (0–50 µg/100 g)
Broccoli:
Vascular bundle in stem:
  200–5,000 µg/100 g (0–100 µg/100 g)
Pithy tissue in stem:
  200–5,000 µg/100 g (0–100 µg/100 g)
Root: 20–1,000 µg/100 g (0–9 µg/100 g)
Seeds: 100–5,000 µg/100 g (0–50 µg/100 g)

Details of the color tone of these parts are as follows. (In parentheses are the color tone of corresponding parts of a corresponding conventional plant.)

Cabbage:
Head-forming leaves inside the head:
  dark orange-yellow (yellow-white)
Petiole of head-forming leaves:
  dark orange-yellow (white)
Vascular bundle in stem:
  reddish orange-light orange (white)
Pithy tissue in stem:
  reddish orange-light orange (white)
Root: orange-light orange (white)
Seeds: orange-dark yellow (yellow)
Chinese kale:
Vascular bundle in stem:
  reddish orange-light orange (white-light green)
Pithy tissue in stem:
  reddish orange-light orange (white-light green)
Root: orange-light orange (white)
Seeds: light orange-dark yellow (yellow)
Kohlrabi:
Inside of the corm:
  dark orange-light orange (white-light green)
Vascular bundle in stem:
  reddish orange-light orange (white-light green)
Pithy tissue in stem:
  reddish orange-light orange (white-light green)
Root: orange-light orange (white)
Seeds: light orange-dark yellow (yellow)
Brussels sprouts:
Head-forming leaves inside the head:
  reddish orange-light orange (yellow-white)
Petiole of head-forming leaves:
  dark orange-yellow (white)
Vascular bundle in stem:
  reddish orange-light orange (white-light green)
Pithy tissue in stem:
  reddish orange-light orange (white-light green)
Root: orange-light orange (white)
Seeds: light orange-dark yellow (yellow)
Kale:
Vascular bundle in stem:
  reddish orange-light orange (white)
Pithy tissue in stem:
  reddish orange-light orange (white)
Root: orange-light orange (white)
Seeds: light orange-dark orange (yellow)
Savoy cabbage:
Head-forming leaves inside the head:
  dark orange-yellow (yellow-white)
Petiole of head-forming leaves:
  dark orange-yellow (white)
Vascular bundle in stem:
  reddish orange-light orange (white)
Pithy tissue in stem:
  reddish orange-light orange (white)
Root: orange-light orange (white)
Seeds: light orange-dark yellow (yellow)
Broccoli:
Vascular bundle in stem:
  reddish orange-light orange (white-light green)
Pithy tissue in stem:
  reddish orange-light orange (white-light green)
Root: orange-light orange (white)
Seeds: light orange-dark yellow (yellow)

The plant of the present invention belonging to *Brassica oleracea* can be obtained by crossing a variety of cauliflower having Or gene with a plant belonging to *Brassica oleracea* having at least one conditioning gene which promotes the expression of Or gene. No special method is required for the crossing, which may be carried out according to conventional methods. Also, with respect to the cultivation of the resultant plant, no special method is required. The plant may be cultured according to conventional methods. The resultant $F_1$ individuals have the following characteristics as well as a high carotene content:

The plant body becomes bigger.

The leaf color becomes darker.

Flower bud differentiation stage comes earlier, and flower stalk development and flowering begin earlier.

It should be noted that the plant of the present invention belonging to *Brassica oleracea* includes not only thus obtained $F_1$ individuals, but also those plants of the subsequent generations obtained by selfing, backcrossing, etc. of the $F_1$ individuals.

Examples of the plant of the present invention belonging to *Brassica napus* include rape, rutabaga and hakuran. The plant of the present invention belonging to *Brassica napus* has a gene which makes the color of a cauliflower curd orange, and preferably, also has a conditioning gene which promotes the expression of the above-mentioned gene.

The characteristics of the plant of the present invention belonging to *Brassica napus* reside in that it contains a large quantity of carotene in at least one of those parts where a conventional *Brassica napus* contains little carotene, and thereby exhibits orange color, light orange color or the like. Examples of such a part include, for rape, vascular bundle in stem, pithy tissue in stem, root, seeds, etc.; and for hakuran, head-forming leaves inside the head, the petiole of head-forming leaves, vascular bundle in stem, pithy tissue in stem, root, seeds, etc.

The approximate carotene contents of these parts are as follows. (In parentheses are values for corresponding parts of a corresponding conventional plant.)

Rape:
Vascular bundle in stem:
200–5,000 μg/100 g (0–100 μg/100 g)
Pithy tissue in stem:
200–5,000 μg/100 g (0–100 μg/100 g)
Root: 20–1,000 μg/100 g (0–9 μg/100 g) Seeds: 100–5,000 μg/100 g (0–50 μg/100 g)

Hakuran:
Head-forming leaves inside the head:
150–5,000 μg/100 g (0–100 μg/100 g)
Petiole of head-forming leaves:
50–5,000 μg/100 g (0–20 μg/100 g)
Vascular bundle in stem:
50–5,000 μg/100 g (0–20 μg/100 g)
Pithy tissue in stem:
50–5,000 μg/100 g (0–20 μg/100 g)
Root: 20–1,000 μg/100 g (0–9 μg/100 g)
Seeds: 100–5,000 μg/100 g (0–50 μg/100 g)

Details of the color tone of these parts are as follows. (In parentheses are the color tone of corresponding parts of a corresponding conventional plant.)

Rape:
Vascular bundle in stem:
reddish orange-light orange (white-light green)
Pithy tissue in stem:
reddish orange-light orange (white-light green)
Root: orange-light orange (white)
Seeds: light orange-dark yellow (yellow)

Hakuran:
Head-forming leaves inside the head:
light orange-yellow (yellow-white)
Petiole of head-forming leaves:
dark orange-yellow (white)
Vascular bundle in stem:
reddish orange-light orange (white)
Pithy tissue in stem:
reddish orange-light orange (white)
Root: orange-light orange (white)
Seeds: light orange-dark yellow (yellow)

*Brassica napus* is an amphidiploid of an interspecific hybrid between *Brassica oleracea* and *Brassica campestris*. Accordingly, the plant of the present invention belonging to *Brassica napus* can be obtained by crossing a cultivar of cauliflower having Or gene with a plant belonging to *Brassica campestris*, and selecting from the resultant interspecific hybrid such individuals in which chromosome duplication has occurred. A plant belonging to *Brassica campestris* used for this purpose is not particularly limited. For example, a commercial cultivar of Chinese cabbage or turnip which is artificially grown may be used. Since a cauliflower cultivar having Or gene and a *Brassica campestris* plant belong to different species, it is difficult to obtain an interspecific hybrid according to conventional methods. In their crossing, it is preferable to remove embryos from the fertilized ovaries and then to carry out embryo culture.

Although chromosome duplication can occur at a certain probability without any artificial treatment, it is possible to increase the number of amphidiploids by selecting them from those redifferentiated individuals which have been obtained by tissue culture of a leaf section; by dripping 0.01–1% aqueous solution of colchicine to the apical meristem of the hybrid individual; or by dipping the plant body in the colchicine solution. With respect to the method for selecting amphidiploids, their plant bodies are bigger than diploids; they have pollen fertility; and they can be selected by observing the chromosome number in root apex cells. The amphidiploids obtained by the above procedures usually have seed fertility, and thus it is possible to maintain subsequent generations by selfing, backcrossing, open pollination, and so on.

Further, the introduction of a conditioning gene which promotes the expression of Or gene can be performed by crossing the amphidiploid obtained by the above procedures with a *Brassica oleracea* plant having at least one conditioning gene which promotes the expression of Or gene. Alternatively, the introduction can be performed by crossing a *Brassica oleracea* plant having Or gene and at least one conditioning gene which promotes the expression of Or gene, with a *Brassica campestris* plant, and selecting from the resultant interspecific hybrid those individuals in which chromosome duplication has occurred. There is no particular limitation in the kind of *Brassica campestris* plant used here. For example, a commercial cultivar of Chinese cabbage or turnip which is artificially grown may be used. Further, the introduction can be performed also by crossing a *Brassica oleracea* plant having Or gene and at least one conditioning gene which promotes the expression of Or gene, with a *Brassica campestris* plant having Or gene and at least one conditioning gene which promotes the expression of Or gene, and selecting from the resultant interspecific hybrid those individuals in which chromosome duplication has occurred.

No special method is required for growing the plant of the present invention belonging to *Brassica napus*. The plant may be grown according to conventional methods. It should be noted here that the plant of the present invention belonging to *Brassica napus* includes not only the above-mentioned interspecific hybrid individuals in which chromosome duplication has occurred, but also plants of the subsequent generations which are obtained by the selfing, backcrossing, etc. of those individuals.

Examples of the plant of the present invention belonging to *Brassica campestris* include Chinese cabbage, turnip and a group of leaf vegetables suitable for pickles, such as leaf mustard and mustard spinach. The plant of the present invention belonging to *Brassica campestris* has a gene (Or gene) which makes the color of a cauliflower curd orange and, preferably, also has a conditioning gene which promotes the expression of Or gene.

The characteristics of the plant of the present invention belonging to *Brassica campestris* reside in that it contains a large quantity of carotene in at least one of those parts where a conventional *Brassica campestris* contains little carotene, and thereby exhibits orange color, light orange color or the like. Examples of such a part include, for Chinese cabbage, head-forming leaves inside the head, the petiole of head-forming leaves, vascular bundle in stem, pithy tissue in stem, root, seeds, etc.; for turnip, vascular bundle in stem, pithy tissue in stem, root, seeds, etc.; and for komatsuna (*Brassica rapa* var. pervidis), vascular bundle in stem, pithy tissue in stem, root, seeds, etc.

The approximate carotene contents of these parts are as follows. (In parentheses are values for corresponding parts of a corresponding conventional plant.)

Chinese cabbage:
Head-forming leaves inside the head:
100–5,000 µg/100 g (0–50 µg/100 g)
Petiole of head-forming leaves:
50–5,000 µg/100 g (0–20 µg/100 g)
Vascular bundle in stem:
50–5,000 µg/100 g (0–20 µg/100 g)
Pithy tissue in stem:
50–5,000 µg/100 g (0–20 µg/100 g)
Root: 20–1,000 µg/100 g (0–9 µg/100 g)
Seeds: 100–5,000 µg/100 g (0–50 µg/100 g)
Turnip:
Root: 20–1,000 µg/100 g (0–9 µg/100 g)
Seeds: 100–5,000 µg/100 g (0–50 µg/100 g)
Komatsuna:
Root: 20–1,000 µg/100 g (0–9 µg/100 g)
Seeds: 100–5,000 µg/100 g (0–50 µg/100 g)

Details of the color tone of these parts are as follows. (In parentheses are the color tone of corresponding parts in a corresponding conventional plant.)
Chinese cabbage:
Head-forming leaves inside the head:
dark orange-yellow (yellow-white)
Petiole of head-forming leaves:
dark orange-yellow (white)
Vascular bundle in stem:
reddish orange-light orange (white-light green)
Pithy tissue in stem:
reddish orange-light orange (white-light green)
Root: orange-light orange (white)
Seeds: light orange-dark yellow (yellow)
Turnip:
Vascular bundle in stem:
reddish orange-light orange (white-light green)
Pithy tissue in stem:
reddish orange-light orange (white-light green)
Root: orange-light orange (white)
Seeds: light orange-dark yellow (yellow)
Komatsuna:
Vascular bundle in stem:
reddish orange-light orange (white-light green)
Pithy tissue in stem:
reddish orange-light orange (white-light green)
Root: orange-light orange (white)
Seeds: light orange-dark orange (yellow)

The plant of the present invention belonging to *Brassica campestris* can be obtained by crossing a cauliflower cultivar having Or gene with a plant belonging to *Brassica campestris*, repeating the backcrossing of the resultant interspecific hybrid, and then selecting those individuals exhibiting orange color. The *Brassica campestris* plant used for this purpose is not particularly limited. For example, a commercial cultivar of Chinese cabbage or turnip which is artificially grown may be used. Since a cauliflower cultivar having Or gene and a *Brassica campestris* plant belong to different species, it is difficult to obtain an interspecific hybrid according to conventional methods. In their crossing, it is preferable to remove embryos from the fertilized ovaries and then to carry out embryo culture. With respect to the method for selecting individuals exhibiting orange color, seedlings which exhibit orange color at the joint part between main stem and petiole, in the vascular bundle at the base of petiole when broken off from main stem, etc. are selected.

The introduction of a conditioning gene which promotes the expression of Or gene can be performed by crossing the individual selected according to the above procedures with a *Brassica oleracea* plant having at least one conditioning gene which promotes the expression of Or gene. Alternatively, the introduction can be performed by crossing a *Brassica oleracea* plant having Or gene and at least one conditioning gene which promotes the expression of Or gene, with a *Brassica campestris* plant.

No special method is required for growing the plant of the present invention belonging to *Brassica campestris*. The plant may be grown according to conventional methods.

Examples of the plant of the present invention belonging to *Raphanus sativus* include Japanese radish. The plant of the present invention belonging to *Raphanus sativus* has a gene (Or gene) which makes the color of a cauliflower curd orange, and, preferably, also has a conditioning gene which promotes the expression of Or gene.

The characteristics of the plant of the present invention belonging to *Raphanus sativus* reside in that it contains a large quantity of carotene in at least one of those parts where a conventional *Raphanus sativus* contains little carotene, and thereby exhibits orange color, light orange color or the like. Examples of such a part include, for Japanese radish, root and seeds. The approximate carotene contents of these parts are as follows. (In parentheses are values for corresponding parts of conventional Japanese radish.)
Japanese radish:
Root: 20–1,000 µg/100 g (0–9 µg/100 g)
Seeds: 100–5,000 µg/100 g (0–50 µg/100 g)

Details of the color tone of these parts are as follows. (In parentheses are the color tone of corresponding parts of conventional Japanese radish.)
Japanese radish:
Root: orange-light orange (white)
Seeds: light orange-dark yellow (yellow)

The plant of the present invention belonging to *Raphanus sativus* can be obtained by crossing a cauliflower cultivar having Or gene with a plant belonging to *Raphanus sativus*, repeating the backcrossing of the resultant interspecific hybrid, and then selecting those individuals which exhibit orange color. The *Raphanus sativus* plant used for this purpose is not particularly limited. For example, a cultivar of Japanese radish which is available as a commercial product may be used. In the above-mentioned crossing and backcrossing, it is preferable to remove embryos from fertilized ovaries and then to carry out embryo culture. With respect to the method for selecting individuals exhibiting orange color, seedlings which exhibit orange color at the joint part between main stem and petiole, in the vascular bundle at the base of petiole when broken off from main stem, in root, etc. are selected. With respect to the introduction of a conditioning gene which promotes the expression of Or gene, it can be performed by crossing the individual selected by the above procedures with a *Brassica oleracea* plant having at least one conditioning gene which promotes the expression of Or gene. Alternatively, this introduction can be performed by crossing a *Brassica oleracea* plant having Or gene and at least one conditioning gene which promotes the expression of Or gene, with a *Raphanus sativus* plant.

No special method is required for growing the plant of the present invention belonging to *Raphanus sativus*. The plant may be grown according to conventional methods.

REFERENCE EXAMPLE

The present inventors grew the orange cauliflower NY163 inbred line (OrOr) in 1989. The properties of this orange cauliflower are shown in Table 1.

TABLE 1

Properties of Cauliflower NY163 Inbred Line

| Properties | Control Cauliflower | NY 163 |
|---|---|---|
| Days needed for maturing (average) | 60–90 | 105 |
| Dia. of curd (cm) | 13–18 | 3.5 |
| Color of curd | White | Orange |
| Genotype of Or gene | oror | OrOr |
| Plant vigor | Standard | Very weak |

The color tone of curds in the tested orange cauliflower was classified into orange, and there were no light orange or dark orange curds observed. The size of curds, which was about 3–4 cm on average, varied rather greatly. Two individuals which had the largest curds were selected, and maintained separately by selfing as line Nos. OC1 and OC2.

In February 1993, the present inventors sowed seeds of the selfed 3rd generation of the above-mentioned two lines. After permanent planting of the resultant seedlings, the color tone and the like were examined in June for each part of the plant bodies. The results are shown in Table 2.

TABLE 2

| Line No. | OC1 | OC2 |
|---|---|---|
| No. of individuals examined | 37 | 39 |
| Color of curd: | | |
| orange | 37 | 39 |
| white | 0 | 0 |
| Cross section of main stem: | Both OC1 and OC2 lines have light orange vascular bundle, and their cross sections also exhibit light orange color. No variation was observed in the color tone. | |

With respect to the two lines examined, the entire cross section of the main stem was stained light orange and the vascular bandle was also light orange. There was no variation in color tone, and all of the individuals in the two lines exhibited a uniform color. The curd was about 4 cm in size on the average, and its color was orange. No light orange nor dark orange curds were observed.

PREFERRED EMBODIMENT OF THE INVENTION

The present invention will now be described in more detail with reference to the following examples, which should not be construed as limiting the scope of the present invention.

Example 1

In the spring of 1990, crossing was carried out using a cabbage purebred line "a" as female parent and an orange cauliflower line as male parent. The resultant $F_1$ individuals exhibited half-formed heads.

In January, 1991, the half-formed head was cut and examined. Flower buds had already been formed therein, and these flower buds and head-forming leaves around them exhibited light orange color. From this result, it was newly found that the Or gene of the orange cauliflower is dominantly expressed in cabbage also, and that both flower buds and head-forming leaves exhibit light orange color.

In the spring of 1991, $F_1$ generation was crossed within itself. Also, $F_1$ generation was backcrossed with cabbage purebred lines "a" and "b" as male parent. In December of the same year, each individual of the selfed generation (i.e., $F_2$) and the backcrossed generation (i.e., $BC_1F_1$) was examined for the presence of orange color in the cross section of the main stem and for the intensity of the color.

In $F_2$ and $BC_1F_1$ generations, there were no such individuals exhibiting light orange color throughout the entire main stem cross section as seen in the above-mentioned orange cauliflower, but there were some individuals wherein only the vascular bundle exhibited light orange color. In addition, there were individuals whose vascular bundle exhibited an orange color darker than light orange, and individuals wherein the entire cross section of the main stem was orange. Accordingly, it was considered that a conditioning gene which promotes the expression of Or gene is present in the cabbage purebred lines "a" and "b", because:

In $F_2$ (the selfed generation of $F_1$ individuals obtained by crossing the cabbage purebred line "a" and an orange cauliflower line) and in $BC_1F_1$ (obtained by backcrossing $F_1$ individuals with the cabbage purebred lines "a" and "b"), some individuals appear whose main stem cross section exhibits a darker orange color than that of orange cauliflower itself;

The color of $BC_1F_1$ individuals segregates into orange, light orange and white; and No gene which expresses orange color has been found in cabbage.

Then, the present inventors have built up the following hypotheses, and carried out $X^2$ test for each of them:

Hypothesis 1.

Inheritance of orange color is completely dominant, being controlled by one gene. ($F_2$ segregation ratio is 3:1; $BC_1F_1$ segregation ratio is 1:1.)

Hypothesis 2.

Inheritance of orange color is incompletely dominant, being controlled by one gene. ($F_2$ segregation ratio is 1:2:1; $BC_1F_1$ segregation ratio is 1:1.)

Hypothesis 3.

Inheritance of orange color is dominant, being controlled by two genes. ($F_2$ segregation ratio is 9:3:4 or 10:2:4; $BC_1F_1$ segregation ratio is 1:1, 1:1:2 or 3:1:4.)

With respect to the standard for the intensity of color, the color of a cross-section of the main stem (including vascular bundle) in orange cauliflower is set as "light orange", and any darker orange color than this is designated "orange". In addition, the judgment of color was carried out without discriminating those cross-sections which are colored all over from those cross-sections which are colored only in the vascular bundle. The results are shown in Tables 3 and 4.

TABLE 3

$\chi^2$ Test for Segregation Ratio in $F_2$ Generation

| $F_2$ Line No. | Color of the Main Stem | | | | Segregation ratio in $F_2$[1] | | | |
|---|---|---|---|---|---|---|---|---|
| | Orange | Light-orange | Color-less | Total | 3:1 | 1:2:1 | 9:3:4 | 10:2:4 |
| 1 | 11 | 3 | 34 | 48 | 53.8x | 58.8x | 53.8x | 53.7x |
| 6 | 6 | 2 | 37 | 45 | 78.6x | 80.1x | 78.6x | 78.7x |
| 7 | 7 | 11 | 33 | 51 | 42.9x | 43.0x | 48.8x | 54.9x |
| 9 | 7 | 2 | 36 | 45 | 72.6x | 74.7x | 72.6x | 72.7x |
| 4 | 25 | 7 | 20 | 52 | 5.03x | 28.7x | 5.16 | 5.54 |
| 8 | 18 | 3 | 23 | 44 | 17.5x | 34.0x | 18.3x | 17.5x |
| 2 | 34 | 8 | 8 | 50 | 2.16 | 50.2x | 3.05 | 2.35 |
| 3 | 29 | 6 | 13 | 48 | 0.11 | 37.7x | 1.23 | 0.117 |
| 5 | 22 | 6 | 11 | 39 | 0.214 | 24.9x | 0.396 | 0.651[2] |

1) Segregation ratio in $F_2$

3:1 In the case of the inheritance of orange color being controlled by dominant Or gene alone.

1:2:1 In the case of the inheritance of orange color being controlled by incompletely dominant Or gene alone.

9:3:4 In the case of the inheritance of orange color being controlled by Or gene and a dominant conditioning gene A, and individuals having Or gene but not the conditioning gene A exhibiting light orange color.

10:2:4 In the case of the inheritance of orange color being controlled by Or gene and a dominant conditioning gene A, and only those individuals whose genotype is Ororaa exhibiting light orange color.

2) Since the theoretical frequency for one class was 5 or below, there was a danger that the degree of significance might become too high in the result of the test. Accordingly, significance test with Yates' correction was also carried out for each class [c=(|d|0.5)÷σ, where d is deviation and σ is standard deviation]. As a result, Line No. 5 was congruent with the ratio 10:2:4. Therefore, the results of $\chi^2$ test agreed with the results of significance test with Yates' correction.

3) $\chi^2 0.05=3.84$ (Degree of freedom=1)

$\chi^2 0.05=5.99$ (Degree of freedom=2)

TABLE 4

$\chi^2$ Test for Segregation Ratio in $BC_1 F_1$ Generation

| $BC_1 F_1$ Line No. | Color of the Main Stem | | | | Segregation ratio in $BC_1 F_1$[1] | | |
|---|---|---|---|---|---|---|---|
| | Orange | Light-orange | Color-less | Total | 1:1 | 1:1:2 | 3:1:4 |
| 3 ($F_1 \times a$) | 6 | 6 | 42 | 54 | 16.7x | | |
| 4 ($F_1 \times a$) | 13 | 11 | 21 | 45 | 0.2 | 0.378 | 6.13x |
| 1 ($F_1 \times a$) | 22 | 3 | 17 | 42 | 1.52 | 18.7x | 4.21 |
| 5 ($F_1 \times a$) | 12 | 10 | 24 | 46 | 0.870 | 0.261 | 4.78 |
| 2 ($F_1 \times b$) | 16 | 4 | 19 | 39 | 0.0256 | 7.41x | 0.2992 |

1) Segregation ratio in $BC_1 F_1$

If Or gene alone controls the inheritance of orange color, the genotype of $F_1$ is Oror and that of cabbage is oror. Then, the segregation ratio in $BC_1 F_1$ genotype is Oror:oror=1:1, i.e., light orange:colorless=1:1, without any variation in the color tone.

If a dominant conditioning gene A is present which makes the color expressed by Or gene darker, there are three possible genotypes for $F_1$ (OrorAA, OrorAa and Ororaa), and also three possible genotypes for cabbage (ororAA, ororAa and ororaa). Through the combination of these genotypes, 9 kinds of $BC_1 F_1$ individuals are obtained, and the segregation ratio in $BC_1 F_1$ falls under one of the following three ratios: 1:1, 1:1:2, 3:1:4.

2) Since the theoretical frequency for one class was 5 or below, there was a danger that the degree of significance might become too high in the result of the test. Accordingly, significance test with Yates' correction was also carried out for each class [c=(|d|0.5)÷σ, where d is deviation and σ is standard deviation]. As a result, Line No. 2 was congruent with the ratio 3:1:4. Therefore, the results of $\chi^2$ test agreed with the results of significance test with Yates' correction.

3) $\chi^2 0.05=3.84$ (Degree of freedom=1)

$\chi^2 0.05=5.99$ (Degree of freedom=2)

As shown in Table 3, there were lines which are not consistent with Hypothesis 1 (i.e., the inheritance of orange color is completely dominant, being controlled by one gene, and $F_2$ exhibits the segregation ratio of 3:1), and also lines which were consistent with the above hypothesis. Since the frequency of occurrence of orange color was low in the hypothesis-consistent lines, they were considered to have a gene which suppresses the expression of Or gene. Further, it was considered that the gene which suppresses the expression of Or gene must be recessive, since in all of the $F_1$ individuals investigated, flower buds and head-forming leaves around them were light orange. The lines congruent with the hypothesis that $F_2$ segregation ratio is 3:1 were not congruent with hypothesis that $F_2$ exhibits the segregation ratio of orange:light orange:colorless=1:2:1. Therefore, Hypothesis 2 (i.e., the inheritance of orange color is incompletely dominant, being controlled by one gene) was abandoned. In addition, it was noticed that the number of those individuals exhibiting the same light orange color as seen in orange cauliflower whose genotype is OrOr was rather small, and that a large number of individuals exhibited darker orange color than that of cauliflower.

In $BC_1 F_1$ generation, as shown in Table 4, 4 lines out of 5 were consistent with Hypothesis 1 (i.e., $BC_1 F_1$ segregation ratio is 1:1). In the remaining 1 line, the occurrence of orange color was extremely low, and it was considered that a gene which suppresses the expression of Or gene was taking part. If Or gene alone controls the inheritance of orange color, then $BC_1 F_1$ individuals must be segregated into light orange and white, and not into orange. However, in the 4 lines consistent with the hypothesis that the segregation ratio is 1:1, colored individuals were further classified into orange and light orange.

Since the hypothesis that the inheritance of orange color is incompletely dominant and is controlled by one gene was abandoned from the results so far mentioned, the inventors have assumed a dominant gene (A) which makes the orange color darker when Or gene is present. Then, $F_2$ segregation ratios based on this hypothesis are 9:3:4 and 10:2:4, with which ratios the $F_2$ lines were very consistent. In addition, based on this hypothesis, there are two possible $BC_1F_1$ segregation ratios into three colors, i.e., 1:1:2 (OrorAa× ororaa) and 3:1:4 (OrorAa×ororAa). $BC_1F_1$ lines were very consistent with this hypothesis.

Accordingly, it has been found that the cabbage purebred line "a" has a gene which suppresses the expression of Or gene and a conditioning gene which promotes the expression of Or gene. From 2 $F_2$ lines whose segregation ratio was 3:1 in the color of the main stem, one individual was selected respectively which had a cabbage shape and exhibited orange color in the vascular bundle, and $F_3$ seeds were obtained therefrom. In the thus obtained $F_3$ generation, the segregation ratio of orange:light orange:colorless was also examined. The results are shown in Table 5.

Or gene and homozygous in the conditioning gene which promotes the expression of Or gene.

In the spring of 1992, individuals which exhibited orange color in the main stem and had a cabbage shape were selected from $BC_1F_1$ generation and crossed within themselves. In the summer of the same year, the resultant $BC_1F_1$ seeds were sown, and a similar investigation was carried out with respect to the segregation ratio of orange color in $BC_1F_2$. The results are shown in Table 6.

TABLE 5

$\chi^2$ Test for Segregation Ratio in $F_3$ Generation

| $F_3$ Line No. | Color. of Main Stem in $F_2$ Indi. | Color of the Main Stem | | | | Segregation ratio in $F_3$[1] | | | |
|---|---|---|---|---|---|---|---|---|---|
| | | Orange | Light-orange | Color-less | Total | 3:1 | 1:2:1 | 9:3:4 | 10:2:4 |
| 19 | Orange | 52 | 0 | 22 | 74 | 0.883 | 98.3x | 17.1x | 10.6x |
| 20 | Orange | 36 | 0 | 9 | 45 | 0.6 | 77.4x | 13.4x | 8.28x |

1) Segregation ratio in $F_3$: the same as that in $F_2$

TABLE 6

$\chi^2$ Test for Segregation Ratio in $BC_1 F_2$ Generation

| $BC_1 F_2$ Line No. | Color of the Main Stem | | | | Segregation ratio in $BC_1 F_2$[1] | | | |
|---|---|---|---|---|---|---|---|---|
| | Orange | Light-orange | Color-less | Total | 3:1 | 1:2:1 | 9:3:4 | 10:2:4 |
| 13 ($F_1$ × a) Selfing | 29 | 5 | 27 | 61 | 12.1x | | | |
| 14 ($F_1$ × a) Selfing | 23 | 3 | 27 | 53 | 19.0x | | | |
| 15 ($F_1$ × a) Selfing | 42 | 10 | 23 | 75 | 1.28 | 49.96x | 2.14 | 151 |
| 16 ($F_1$ × a) Selfing | 30 | 7 | 11 | 48 | 0.11 | 39.12x | 0.86 | 0.25 |
| 17 ($F_1$ × a) Selfing | 33 | 11 | 13 | 57 | 0.15 | 35.53x | 0.17 | 2.41 |
| 11 ($F_1$ × b) Selfing | 34 | 5 | 9 | 48 | 1 | 56.12x | 4.34 | 1.45 |
| 12 ($F_1$ × b) Selfing | 33 | 5 | 11 | 49 | 0.17 | 50.80x | 3.11 | 0.51 |

2) $\chi^2 0.05=3.84$ (Degree of freedom=1)
$\chi^2 0.05=5.99$ (Degree of freedom=2)

As shown in the Table, in both lines of $F_3$, there were no individuals exhibiting light orange color in the vascular bundle of the main stem. There were only those which exhibited orange color or those which were colorless. When $\chi^2$ test was carried out to determine whether these lines were consistent with the hypothesized segregation ratio (orange:colorless) of 3:1, both lines were found to be consistent with this ratio. Accordingly, it was presumed that the genotype of parent individuals had been heterozygous in 1) Segregation ratio in $BC_1F_2$
3:1 In the case of the inheritance of orange color being controlled by dominant Or gene alone.
2:1 In the case of the inheritance of orange color being controlled by incompletely dominant Or gene alone.
9:3:4 In the case of the inheritance of orange color being controlled by Or gene and a dominant conditioning gene A, and individuals having Or gene but not the conditioning gene A exhibiting light orange color.
10:2:4 In the case of the inheritance of orange color being controlled by Or gene and a dominant conditioning gene A, and only those individuals whose genotype is Ororaa exhibiting light orange color.

2) $\chi^2 0.05=3.84$ (Degree of freedom=1)
$\chi^2 0.05=5.99$ (Degree of freedom=2)

When the cabbage purebred line "a" was used as backcross parent, 2 lines out of 5 were not congruent with the hypothesis that the segregation ratio is 3:1, and the ratio of white to colored was higher than 1:3. Thus, the presence of a gene which suppresses the expression of Or gene was considered. The remaining three lines were congruent with the hypothesis that the segregation ratio is 3:1, but the hypothesis of a 1:2:1 segregation ratio was abandoned. On the other hand, as these three lines were consistent with the hypotheses that segregation ratios are 9:3:4 and 10:2:4, the presence of Or gene and a conditioning gene which makes darker the color expressed by Or gene was considered.

When the cabbage purebred line "b" was used as backcross parent, both daughter lines were congruent with the hypothesis that the segregation ratio is 3:1, but the hypothesis of 1:2:1 segregation ratio was abandoned. These results supported the hypothesis that the inheritance of orange color is not controlled by one incompletely dominant gene. Further, since both lines were congruent with the hypotheses that segregation ratios are 9:3:4 and 10:2:4, the presence of Or gene and a conditioning gene which promotes the expression of Or gene were considered.

From the above-mentioned results, it was found that the cabbage purebred line "a" has a gene which suppresses Or gene and, at the same time, a conditioning gene which promotes the expression of Or gene, while the cabbage purebred line "b" has the conditioning gene which promotes the expression of Or gene but not the gene which suppresses Or gene.

In the spring of 1992, those individuals which exhibited orange color in the main stem and had a cabbage shape were selected from $BC_1F_1$ generation. These individuals were backcrossed with cabbage purebred lines "a", "b", "c" and "d" to thereby obtain $BC_2F_1$ seeds. In the summer of the same year, these seeds were sown and a similar investigation was carried out with respect to the segregation of orange color in $BC_2F_1$ generation. The results are shown in Table 7.

TABLE 7

$\chi^2$ Test for Segregation Ratio in $BC_2 F_1$ Generation

| $BC_2 F_1$ Line No. | Color of the Main Stem | | | | Segregation ratio in $BC_2 F_1$[1] | | |
|---|---|---|---|---|---|---|---|
| | Orange | Light-orange | Color-less | Total | 1:1 | 1:1:2 | 3:1:4 |
| 3 ($F_1 \times$ a) | 16 | 3 | 25 | 44 | 0.82 | 8.50x | 1.56 |
| 4 ($F_1 \times$ a) | 10 | 11 | 27 | 48 | 0.75 | 0.79 | 8.10x |
| 5 ($F_1 \times$ a) | 17 | 10 | 21 | 48 | 0.75 | 2.79 | 3.10 |
| 6 ($F_1 \times$ a) | 7 | 13 | 33 | 53 | 3.19 | 4.55 | 3.99 |
| 7 ($F_1 \times$ b) | 19 | 8 | 19 | 46 | 1.39 | 6.65x | 1.90 |
| 1 ($F_1 \times$ c) | 14 | 1 | 24 | 39 | 2.08 | 10.74x | 4.15[2] |
| 2 ($F_1 \times$ c) | 24 | 0 | 13 | 37 | 3.27 | 34.41x | 13.65x[2] |
| 8 ($F_1 \times$ d) | 25 | 0 | 23 | 48 | 0.083 | 26.12x | 8.76x |
| 9 ($F_1 \times$ d) | 13 | 5 | 19 | 37 | 0.027 | 3.49 | 0.099[2] |
| 10 ($F_1 \times$ d) | 20 | 4 | 20 | 44 | 0.36 | 11.9x | 1.33 |

1) Segregation ratio in $BC_2F_1$ generation
If Or gene alone controls the inheritance of orange color, the genotype of $BC_1F_1$ is Oror and that of cabbage is oror. Then, the segregation ratio in $BC_2F_1$ genotype is Oror:oror= 1:1, i.e., light orange:colorless=1:1, without any variation in the color tone.

If a dominant conditioning gene A is present which makes the color expressed by Or gene darker, there are three possible genotypes for $BC_2F_1$ (OrorAA, OrorAa and Ororaa), and also three possible genotypes for cabbage (ororAA, ororAa and ororaa). Through the combination of these genotypes, 9 kinds of $BC_2F_1$ individuals are obtained, and the segregation ratio in $BC_2F_1$ falls under one of the following three ratios: 1:1, 1:1:2, 3:1:4.

2) Since the theoretical frequency for one class was 5 or below, there was a danger that the degree of significance might become too high in the result of the test. Accordingly, significance test with Yates' correction was also carried out for each class [c=(|d|0.5)÷σ, where d is deviation and σ is standard deviation]. As a result, Line No. 1 and Line No. 9 were congruent with the ratio 3:1:4, and Line NO. 2 was not congruent with the same. Therefore, the results of $\chi^2$ test agreed with the results of significance test with Yates' correction.

3) $\chi^2 0.05=3.84$ (Degree of freedom=1)
$\chi^2 0.05=5.99$ (Degree of freedom=2)

All of the 4 daughter lines wherein the cabbage purebred line "a" had been used as backcross parent were consistent with the hypothesis that the segregation ratio is 1:1, but these 4 daughter lines into three colors of orange, light orange and white. These 4 lines were congruent with the segregation ratio of 1:1:2 or 3:1:4 which is based on the hypothesis that both Or gene and a conditioning gene which promotes the expression of Or gene are present. The only one line wherein the cabbage purebred line "b" had been used as backcross parent also segregated into three colors of orange, light orange and white. This line was consistent with the segregation ratios of 1:1 and 3:1:4. The lines wherein the cabbage purebred line "c" had been used as backcross parent were consistent with the 1:1 ratio, and in one of them there were no light orange individuals. In both lines, the hypothesis that the segregation ratio is 1:1:2 was abandoned. Although Line No. 1 was congruent with the hypothesis that the segregation ratio is 3:1:4, this hypothesis was abandoned for line No. 2, but found to be consistent with Line No. 1. All the 3 lines wherein the cabbage purebred line "d" had been used as backcross parent were congruent with the segregation ratio of 1:1. In one of these three lines, there were no light orange individuals. In another of these three lines, the hypothesis that the segregation ratio is 1:1:2 was abandoned and this line was consistent with the segregation ratio of 3:1:4. The remaining of these three line was congruent with both the hypothesis of 1:1:2 and that of 3:1:4. From these results, it was found that all of the cabbage purebred lines "a", "b", "c" and "d" have a conditioning gene which promotes the expression of Or gene.

Example 2

Carotene contents were measured on conventional cabbage cultivars (i.e., those having no Or gene) and cabbage cultivars having Or gene and being Oror in genotype.

The measurement of carotene content was carried out as follows.

Carotene component, which is mainly composed of β-carotene, was fractionated from the other pigment components by alumina chromatography using 2% acetone-n-hexane as an eluent. The solution obtained was distilled under reduced pressure, and the residues were dissolved in n-hexane. Absorbance at 453 nm was measured with a spectrophotometer using n-hexane as control. The quantitative value were calculated from the calibration curve of β-carotene standard solution. Since β-carotene was used as the standard substance, the quantitative value was obtained as a total quantity of carotenes converted into β-carotene. The calculated values were rounded off at the first decimal place and expressed in the form of "n µg" where n is an integer. Values less than 6 µg were represented by φ which means "not zero". Unless otherwise specified, analysis samples were taken as follows. A cabbage was vertically cut from the top center of the head by a width of 1 cm so that all of the head-forming leaves are contained in a sample, and the cut piece obtained was chopped finely and mixed to prepare a sample.

The carotene contents per 100 g of 4 conventional cabbage lines are shown in Table 8.

TABLE 8

Total Carotene Contents in 4 Cabbage Lines (Average)

| Line No. | No. of Individuals | Total Carotene Content (µg/100 g) |
| --- | --- | --- |
| a | 5 | 23 |
| b | 3 | 14 |
| c | 4 | 26 |
| d | 4 | 46 |
| Total | 16 | 27 (average) |

Using these 4 lines as backcross parents, backcrossing of $F_1$ (orange cauliflower×cabbage "a") was carried out twice. In the resultant generation ($BC_2F_1$), 4 lines having Or gene heterozygously were examined for the carotene content per 100 g, and the results are shown in Table 9.

TABLE 9

Total Carotene Contents of Oror Individuals in $BC_2 F_1$ Generation (Average)

| Crossing Combination in $BC_2 F_1$ | No. of Individuals | Total Carotene Content (µg/100 g) |
| --- | --- | --- |
| $(F_1 \times a) \times a$ | 3 | 59 |
| $(F_1 \times b) \times b$ | 2 | 100 |
| $(F_1 \times a) \times c$ | 4 | 72 |
| $(F_1 \times a) \times d$ | 5 | 183 |

Notes)
a,b,c,d: cabbage lines
$F_1$: orange cauliflower × a

From Table 9, it was found that, when Or gene has been introduced into a conventional cabbage line, its carotene content increases by 3–7 times, and that the increasing rate of carotene content varies depending on the line used as backcross parent.

Among the $BC_2F_1$ lines having Or gene heterozygously, the line ($F_1$×a)×d had the highest carotene content. Each individual of this line was examined for the presence of orange color in the cross section of the main stem and the vascular bundle, leaf color at the cross section of the head, and carotene content. The results are shown in Table 10.

TABLE 10

Total Carotene Content per 100 g of Head-Forming Leaves (Fresh) by Individual in ($F_1 \times a$) × d Line

| Indivi. No. | Orange color exhibiting part | Leaf color | Total carotene content (µg/100) |
| --- | --- | --- | --- |
| A) When the sample was prepared from small portions of all the head-forming leaves | | | |
| 1 | All over the cross-section incl. vascular bundle | Yellowish orange | 250 |
| 2 | Vascular bundle | Yellow | 144 |
| 3 | Vascular bundle | Yellow | 190 |
| 4 | None | Yellow | 129 |
| 5 | None | Light yellow | 62 |
| 6 | None | Very light yellow | 55 |
| 7 | None | Very light yellow | 38 |
| (B) When the sample was prepared from one leaf located at the center of head-forming leaves | | | |
| 11 | All over the cross-section incl. vascular bundle | Yellowish orange | 452 |
| 12 | All over the cross-section incl. vascular bundle | Yellowish orange | 433 |
| 13 | All over the cross-section incl. vascular bundle | Yellowish orange | 405 |
| 14 | Vascular bundle | Yellow | 167 |
| 15 | Vascular bundle | Light yellowish orange | 161 |
| 16 | Vascular bundle | Yellow | 136 |
| 17 | None | Light yellow | 170 |
| 18 | None | Light yellow | 69 |
| 19 | None | Light yellow | 60 |
| 20 | None | Light yellow | 58 |
| 21 | None | Very light yellow | 45 |
| 22 | None | Very light yellow | 30 |
| 23 | None | Very light yellow | 25 |
| 24 | None | Very light yellow | 22 |
| 25 | None | Very light yellow | 15 |
| 26 | None | White | 12 |

1) None: The cross-section of the main stem has the same color as that of conventional cabbage.

Since the line ($F_1$×a)×d has been obtained by backcrossing, it has two genotypes of Oror (which exhibits orange color) and oror (which exhibits the same color as that of the conventional cabbage). Even when the color of the main stem cross section was the same as that of the conventional cabbage, there appeared some individuals (Nos. 3 and 17) which had higher carotene contents than those of backcross parent lines "a" and "d" ("a": 23 µg, "d":46 µg). As the leaf color changed in the following order:

white-very light yellow-light yellow-yellow-yellowish orange, acquiring deepening yellow color up to an orange tinge, carotene content increased. In addition, those individuals whose main stem cross-section including vascular bundle was orange all over (leaf color:yellowish orange) had a higher carotene content than those individuals which exhibited orange color only in the vascular bundle at the main stem cross-section (leaf color: yellow or light yellowish orange). As the orange color-exhibiting part varied from no part (same as the conventional cabbage) to the vascular bundle to the entire cross-section including vascular bundle, carotene content increased.

In the line ($F_1$×a)×d which had the highest carotene content, individuals exhibiting orange color all over the main stem cross-section including vascular bundle were selected, and their carotene contents by part were measured. Similar measurement was carried out on conventional cabbages, and the results were compared. Table 11 shows the results.

TABLE 11

Comparison of Total Carotene Content (Average) by Part between Conventional Cabbages and Oror Individuals

| | Conventional cabbages | | $(F_1 \times a) \times d$ individuals | |
|---|---|---|---|---|
| | No. of indivi. examined | Carotene (µg/100 g) | No. of indivi. examined | Carotene (µg/100 g) |
| Around the core | 1 | φ | 1 | 384 |
| Inner leaf rather close to the core | 1 | 39 | 2 | 306 |
| Inner leaf | 1 | 14 | 3 | 243 |
| Inner leaf rather close to the outside | — | — | 1 | 405 |
| Edible, outermost head-forming leaf | 1 | 260 | — | — |
| Petiole of head-forming leaves | 4 | φ | 3 | 617 |
| All of the head-forming leaves | 16 | 27 | 3 | 195 |

In conventional cabbages, the carotene content is 260 µg/100 g at the edible, outermost head-forming leaf but most of the edible head-forming leaves had a low carotene content (0–39 µg/100 g), and the carotene content was almost zero around the core. In contrast, cabbages having Or gene had very high carotene contents of 243–405 µg/100 g at any part of the Or gene containing cabbage.

With respect to the petiole of head-forming leaves, the carotene contents of conventional cabbages were from zero to 11 µg/100 g, while those of cabbages having Or gene were from 22 µg/100 g to 990 µg/100 g. The carotene content of this part increased by 2–90 times.

Example 3

In July, 1989, seeds from 3 lines of Chinese kale and the orange cauliflower NY163 inbred line were sown. In the spring of 1990, a Chinese kale line (female parent) was crossed with NY163. In July of the same year, the resultant crossbred seeds were sown to thereby grow $F_1$ individuals. The morphology of flower buds (edible part) of Chinese kale resembles that of broccoli. Chinese Kale's flower buds look like small buds of broccoli which have slightly grown, and its flower stalks as a whole have an elongated shape. A $F_1$ individual which is a hybrid between Chinese kale and orange cauliflower forms a light orange mass of tissues resembling a flower head, but soon most of the flower buds in the tissue mass grow into small buds (in ordinary cauliflower, a half of the flower buds become dormant or remain undeveloped, and do not form flower stalks). At the same time, the color of the tissue mass changes from light orange to green. This mass of small green buds presents the intermediate morphology between broccoli and Chinese kale.

In the spring of 1991, $F_1$ individuals were crossed within themselves to thereby obtain $F_2$ seeds. Flower heads of $F_2$ individuals were cut off and the color of main stem cross sections was examined, to thereby carry out $\chi^2$ test for the $F_2$ segregation ratio. The results are shown in Table 12.

TABLE 12

$\chi^2$ Test for $F_2$ Segregation Ratio of the Color in the Main Stem Cross-Section

| | Color of the Cross-Section | | | | | | | |
|---|---|---|---|---|---|---|---|---|
| (Chinese kale × NY163)$F_2$ | Orange | Light-orange | Color-less | Total | 3:1 | 1:2:1 | 9:3:4 | 10:2:4 |
| (1) | 27 | 6 | 16 | 49 | 1.53 | 32.9x | 2.27 | 1.58 |
| (2) | 20 | 11 | 16 | 47 | 2.05 | 13.98x | 3.65 | 9.00x |
| (3) | 22 | 9 | 18 | 49 | 3.60 | 20.27x | 3.83 | 6.48x |

1) Segregation ratio in $F_2$

3:1 In the case of the inheritance of orange color being controlled by Or gene alone which is dominant.

1:2:1 In the case of the inheritance of orange color being controlled by Or gene alone which is incompletely dominant.

9:3:4 In the case of the inheritance of orange color being controlled by Or gene and a dominant conditioning gene A, and individuals having Or gene but not the conditioning gene A exhibiting light orange color.

10:2:4 In the case of the inheritance of orange color being controlled by Or gene and a dominant conditioning gene A, and only those individuals whose genotype is Ororaa exhibiting light orange color.

2) $\chi^2 0.05=3.84$ (Degree of freedom=1)
$\chi^2 0.05=5.99$ (Degree of freedom=2)

With respect to the segregation of color in the main stem cross section when the flower head was cut off, the color was classified into orange, light orange and non-orange (i.e., the same color as that of the main stem cross section of Chinese kale). All of the 3 lines of $F_2$ generation were consistent with the hypothesis of the 3:1 segregation ratio based on dominant one gene control. The hypothesis of 1:2:1 segregation ratio based on incompletely dominant one gene control was abandoned, and it was found that the inheritance of orange color is not controlled by one incompletely dominant gene. Since a number of individuals appeared which exhibited an orange color darker than light orange, the presence of a conditioning gene (A) which promotes the expression of Or gene was considered. Then, $\chi^2$ test was carried out for the segregation ratio based on this hypothesis of dominant two gene control, tested lines were very consistent with the ratio of 9:3:4 or 10:2:4.

Example 4

In the spring of 1991, the inventors planned to produce an interspecific hybrid by fertilizing each 4 individuals of 2 Chinese cabbage lines with pollen of 2 individuals of NY163 selfed 1st generation. For each of the female parents, about 1000 flowers were fertilized with pollen, but all of the fertilized ovaries fell off during the seed growth period and no crossbred seed could be obtained. Therefore, it was considered impossible to obtain hybrid seeds according to conventional methods. Then, the inventors decided to remove embryos from fertilized ovaries 2–5 weeks after crossing under sterile conditions to thereby carry out embryo culture, while carrying out conventional crossing simultaneously in the following year.

In the spring of 1992, each individual of 3 Chinese cabbage lines and 1 turnip line were fertilized with pollen of individuals of NY163 inbred 2nd generation. The results obtained according to conventional crossing methods are shown in Table 13, and the results obtained by embryo culture in Table 14.

As shown in Table 13, though crossbred seeds could be obtained by conventional crossing, all of them were found to be matroclinal plants as judged from the state of growth after germination and permanent plantation. As shown in Table 14, in embryo culture, 59 embryos were obtained from 153 fertilized ovaries, and 46 embryos out of 59 germinated. Tissue culture was carried out in such a manner that axillary buds grow from leaf axils during cultivation, to thereby obtain a plurality of clone individuals. A group of clone individuals obtained from one individual which had germinated were designed as one line. Individuals were transplanted from pots from the summer to autumn of 1992. Finally, 8 lines ($F_1$) could be transplanted from pots. From the morphology of seedlings after this transplantation, 7 lines appeared to be matroclinal plants and the remaining one was considered to be an interspecific hybrid ($F_1$ individual).

In the winter of 1993, 10 clone individuals of the line which seemed to be an interspecific hybrid were investigated for their pollen fertility, morphologic characteristics, and the presence of orange color. In addition, their carotene contents in the leaf part were measured. All of these 10 individuals had the intermediate morphology between their parents, producing a half-formed head. There were 9 individuals which did not have pollen fertility. The remaining one had pollen fertility, and was capable of selfing by bud pollination and seed-harvesting by open pollination. In addition, compared to the sterile individuals, the fertile individual was larger in the shapes of leaves and flowers. The chromosome number of this individual was found to be 2n=38. Accordingly, this fertile individual was presumed to be a

TABLE 13

Harvested Amount of Interspecific Crossbred Seeds obtained by Conventional Crossing, and the Characteristics of the Individuals Germinating therefrom

| Crossing combination | No. of female parent | No. of seeds harvested | No. of seeds sown | No. of seeds which germinated | No. of individuals permanently planted | Characteristics after permanent plantation |
|---|---|---|---|---|---|---|
| B × OC[1] | 1 | 3 | 3 | 3 | 3 | Matroclinal |
| C × OC | 6 | 95 | 53 | 45 | 45 | Matroclinal |
| D × OC | 5 | 55 | 55 | 49 | 49 | Matroclinal |
| OC × C | 4 | 890 | 170 | 150 | 80 | Matroclinal |

[1] B, C, D = Chinese cabbage lines OC = NY163 inbred line

TABLE 14

Production of Interspecific Hybrid by Embryo Culture

| Crossing combination | No. of ovaries supplied | No. of embryos cultured | No. of seeds which germinated | No. of individuals $F_1$ transplanted from pots | line No.[2] |
|---|---|---|---|---|---|
| B × OC[1] | 34 | 12 | 12 | 2 | 8,9 |
| C × OC | 4 | 3 | 2 | 2 | 3,5 |
| D × OC | 59 | 36 | 24 | 4 | 1,4,6,7 |
| T × OC | 56 | 8 | 8 | 0 | |
| OC × C | 153 | 59 | 46 | 8 | 8 lines |

[1] B, C, D = Chinese cabbage lines T = Turnip line OC = NY163 inbred line
[2] Nos. 1, 3–8 = matroclinal individuals (Chinese cabbage) No. 9 = interspecific hybrid synthetic Brassica napus whose chromosome had been duplicated during tissue culture, and the remaining 9 individuals an interspecific hybrid between Brassica oleracea and Brassica campestris.

The fertile individual presumed to be a synthetic Brassica napus exhibited very light orange color at the joint between main stem and petiole. Further, inner small leaves surrounded by half-head-forming leaves and all over the cross-section of the root were also light orange.

The carotene content in the selfed seeds of this fertile individual was found to be 209 µg/100 g, a very high content compared to those of conventional rapes (53 µg/100 g in line "a" and 22 µg/100 g in line "b").

In the spring of 1993, the above fertile individual was backcrossed with a Chinese cabbage line, and it was also selfed by bud pollination. The results are shown in Table 15.

TABLE 15

Harvested Amount and Germination Ratio of the Seeds
obtained by the Backcrossing and Selfing of Fertile Individuals

| Crossing combination | No. of seeds harvested | No. of seeds sown | No. of seeds which germinated | Germination ratio (%) |
|---|---|---|---|---|
| No. 9-2 × E[1] | 32 | 0 | — | — |
| Bud pollination (selfing) | 192 | 25 | 25 | 100 |
| Open pollination | 745 | 0 | — | — |

[1]No. 9-2 = Interspecific hybrid fertile individual (2n = 38) E = Chinese cabbage line As shown in Table 15, the fertile individual was capable of selfing by bud pollination, backcrossing with Chinese cabbage, and seed-harvesting by open pollination.

Example 5

Carotene contents were measured for the 9 sterile individuals which were presumed to be an interspecific hybrid between *Brassica oleracea* and *Brassica campestris* in Example 4. In conventional Chinese cabbages, the carotene content was 38 μg/100 g in the leaf part inside the head and 0 μg/100 g in the petiole. In contrast, the carotene content of the sterile individuals in the leaf part inside the half-formed head was 496 μg/100 g, a very high content compared to that of conventional Chinese cabbages. In addition, similar to the fertile individual in Example 4, these sterile individuals also exhibited very light orange color at the joint between main stem and petiole, and further, their inner small leaves surrounded by half-head-forming leaves and all the entire cross-section of their root were also light orange.

In the spring of 1993, the inventors planned to produce $BC_1F_1$ individuals by backcrossing 6 sterile individuals with pollen of 2 Chinese cabbage lines and 1 turnip line. Two processes were employed: one was to leave fertilized ovaries in plant bodies to grow embryos therein, and the other was to remove embryos from fertilized ovaries under sterile conditions 15–30 days after the crossing to thereby carry out embryo culture. The results are shown in Tables 16 and 17.

TABLE 16

Harvested Amount of the Interspecific Crossbred Seeds
obtained by Conventional Crossing and the Germination Ratio

| Crossing combination | No. of seeds harvested | No. of seeds sown | No. of seeds which germinated | Germination ratio (%) |
|---|---|---|---|---|
| No. 9-2 × E[1] | 32 | 0 | — | — |
| Bud pollination (selfing) | 192 | 25 | 25 | 100 |
| Open pollination | 745 | 0 | — | — |
| 3 × E | 2 | 2 | 2 | 100 |
| 5 × E | 1 | 1 | 1 | 100 |
| 6 × E | 2 | 2 | 1 | 50 |
| 6 × F | 6 | 6 | 5 | 83 |
| 8 × E | 6 | 6 | 3 | 50 |
| 8 × F | 9 | 9 | 7 | 78 |
| 10 × E | 21 | 21 | 20 | 95 |
| 10 × U | 62 | 44 | 40 | 91 |

[1]No.9-2 = Interspecific hybrid fertile individual (2n = 38) Nos. 9-3,5,6,8,10 = Interspecific hybrid sterile individuals (2n = 19) E,F = Chinese cabbage lines U = Turnip line

TABLE 17

Production of $BC_1F_1$ Individuals by Embryo Culture

| Crossing combination | No. of ovaries supplied | No. of embryos cultured | No. of seeds which germinated | No. of individuals $BC_1F_1$ transplanted from pots | line No. |
|---|---|---|---|---|---|
| No. 9-6 × $F_1$[1] | 8 | 3 | 3 | 2 | 1,2 |
| No. 9-8 × F | 12 | 9 | 9 | 3 | 3,4,5 |
| Total | 20 | 12 | 12 | 5 | 5 lines |

[1]Nos.9-6 and 9-8 = Interspecific hybrid sterile individuals F = Chinese cabbage line As shown in Table 16, a small quantity of backcrossed seeds could be obtained by conventional crossing. When embryo culture was carried out, 12 embryos were obtained from 20 ovaries, and 4 individuals germinated. Accordingly, $BC_1F_1$ individuals can be obtained from sterile individuals utilizing either conventional backcrossing methods or embryo culture method.

Example 6

In the spring of 1991, the inventors intended to produce an interspecific hybrid by fertilizing each 2 individuals of 5 Japanese radish lines with pollen of 2 individuals from NY163 selfed 1st generation. For each of the parents, 1000 flowers were fertilized, but seeds were hardly obtained except that from one individual of line A, seven seeds were obtained which seemed to be hybrid seeds. In July of the same year, these seeds were sown, and subsequently 3 of them germinated and grew. Although one of them died during the course of growth, the remaining 2 individuals continued growing and reached flowering. Both individuals greatly resembled Japanese radish in the appearance of upper plant body and the shape and color of flowers. They exhibited light green color, and the presence of orange color derived from their male parents could not be confirmed from the outside. Their root did not grow so thick as Japanese radish's, and they had a rather thin main root. However, both individuals had no pollen fertility at all.

In the spring of 1992, the inventors intended to produce $BC_1F_1$ individuals by fertilizing the above-mentioned interspecific hybrid 2 individuals ($F_1$) with pollen from 2 Japanese radish lines. However, all of the fertilized ovaries fell off 20–30 days after the fertilization, and it seemed very difficult to obtain crossbred seeds. Then, it was planned to carry out embryo culture by removing embryos from fertilized ovaries before the fertilized ovaries fell off. Embryos were removed from ovaries 6–30 days after the fertilization under sterile conditions, and cultured. The results are shown in Table 18.

TABLE 18

Production of $BC_1F_1$ Individuals by Embryo Culture

| $BC_1F_1$ Crossing combination | No. of ovaries supplied | No. of embryos cultured | No. of seeds which germinated | No. of individuals transplanted from pots | $BC_1F_1$ line No. |
|---|---|---|---|---|---|
| $F_1$-1 × B-1[1] | 44 | 38 | 17 | 13 | 1–3, 5–14 |
| $F_1$-1 × B-3 | 1 | 1 | 0 | 0 | |
| $F_1$-2 × B-1 | 2 | 2 | 0 | 0 | |

TABLE 18-continued

Production of BC₁ F₁ Individuals by Embryo Culture

| BC₁ F₁ Crossing combination | No. of ovaries supplied | No. of embryos cultured | No. of seeds which germinated | No. of individuals transplanted from pots | BC₁ F₁ line No. |
|---|---|---|---|---|---|
| F₁-2 × C-1 | 27 | 29 | 5 | 2 | 4, 15 |
| Total | 74 | 70 | 22 | 15 | |

[1]F₁ = Japanese radish line A × NY163 inbred line B, C = Japanese radish lines

As shown in Table 18, 70 embryos were obtained from 74 fertilized ovaries, and 22 embryos out of 70 germinated. Tissue culture was carried out in such a manner that axillary buds grew from leaf axils during cultivation, thereby obtaining a plurality of clone individuals. A group of clone individuals obtained from one individual which had germinated were designated as one line. Individuals were transplanted from pots from the summer to autumn of 1992. Finally, 15 lines (BC₁F₁) could be transplanted from pots.

In the winter of 1993, the BC₁F₁ 15 lines were investigated for pollen fertility, morphological characteristics and the presence of orange color. In addition, their carotene contents in the root part were measured. The results are shown in Table 19.

TABLE 19

Characteristics of BC₁ F₁ Lines

| Line No. | No. of clones | Pollen fertility (%) | Presence of orange color, and orange color exhibiting parts | Carotene content[1] |
|---|---|---|---|---|
| 1 | 1 | 34 | — | — |
| 2 | 5 | 43 | Light orange, a part of vascular bundle at the base of the main stem | 41 |
| 3 | 4 | 15 | White | 59 |
| 4 | 2 | — | White | φ[2] |
| 5 | 5 | 0 | Light orange, a part of vascular bundle at the base of the main stem | 87 |
| 6 | 8 | 12 | Light orange, a part of vascular bundle of the base of the main stem, all over the root | 117 |
| 7 | 6 | 6 | White | 38 |
| 8 | 6 | 0 | Light orange, a part of vascular bundle of the base of the main stem, all over the root | 27 |
| 9 | 10 | 0 | Light orange, a part of vascular bundle of the base of the main stem, all over the root | 68 |
| 10 | 2 | 0 | — | — |
| 11 | 4 | 1 | Light orange, a part of vascular bundle of the base of the main stem, all over the root | — |
| 12 | 7 | 0 | Light orange, a part of vascular bundle of the base of the main stem, all over the root | 159 |
| 13 | 8 | 0 | White | φ |
| 14 | 2 | — | Light orange, a part of vascular bundle of the base of the main stem | — |
| 15 | 4 | 0 | White | — |

[1] μg/100 g
[2] φ = not zero, but less than 6 μg/100 g.

As shown in Table 19, most of the lines had no or extremely low pollen fertility but 4 lines out of 15 had pollen fertility. Like F₁ individuals, BC₁F₁ individuals greatly resembled Japanese radish in the appearance of the upper plant body and the shape and color of the flowers. They exhibited strong green color, and the presence of orange color derived from their male parents could not be confirmed from the outside. Their root did not grow so thick as Japanese radish's. They had a rather thin main root, but it had a tendency of being thicker than that of F₁ individuals. One clone individual was selected from each of the 15 lines, and was cut horizontally at several places. Then, several individuals exhibiting light orange color were found. The parts exhibiting orange color were a part of vascular bundle located at the base of the main stem and all over the cross-section of root including medullary tissue and vascular bundle. When the carotene contents of BC₁F₁ 10 lines were measured, 8 lines out of 10 contained carotene. The highest carotene content was 159 μg/100 g and the average content was 75 μg/100 g.

In the spring of 1993, the inventors intended to produce BC₂F₁ individuals by backcrossing 4 lines which seemed to contain carotene because of their light orange color in the root part with pollen of Japanese radishes. The results are shown in Table 20.

TABLE 20

Harvested Amounts and Germination Ratios of BC₂ F₁ Seeds

| Crossing combination | No. of individuals | Total No. of seeds harvested | No. of seeds sown | No. of seeds which germinated | Germination ratio (%) |
|---|---|---|---|---|---|
| No. 1[1] (open pollination) | 1 | 113 | 0 | — | — |
| No. 3 (open pollination) | 1 | 270 | 0 | — | — |
| No. 6 × D | 5 | 219 | 62 | 34 | 55 |
| No. 9 × D | 7 | 198 | 94 | 48 | 51 |
| No. 11 × E | 3 | 32 | 25 | 10 | 40 |
| No. 12 × E | 4 | 116 | 63 | 39 | 62 |

[1] Nos. 1,3,6,9,11,12 = BC₁ F₁ lines D,E = Japanese radish lines

As shown in Table 20, despite the no or extremely low pollen fertility in the 4 lines, crossbred seeds could be obtained. In addition, Line Nos. 1 and 3, the presence of whose orange color was either non-existent or unknown, were capable of producing seeds by open pollination. The backcrossed seeds (BC₂F₁ seeds) harvested in September of the same year were sown, and the germination ratio thereof was about 50%.

What is claimed is:

1. A plant belonging to Brassica napus L., Brassica campestris L., or Raphanus sativus L., having an Or gene.

2. A cultivar of cabbage (B. oleracea L. var. capitata L.), kale (B. oleracea L. var. acephala DC.), kohlrabi (B. oleracea L. var. gongylodes DC.), savoy cabbage (B. oleracea L. var. bullta DC.), Brussels sprouts (B. oleracea L. var. gemmifera Zenk.), broccoli (B. oleracea L. var. italica DC.) or Chinese kale (B. oleracea L. var. alboglabra Bayl.), having an Or gene.

3. The plant of claim 1 wherein the plant is fertile and non-matroclinal.

4. The plant of claim 2 wherein the plant is fertile and non-matroclinal.

5. The plant of claim 1 comprising a plurality of tissues other than a curd which exhibit an external orange or light orange color.

6. The plant of claim 2 comprising a plurality of tissues other than a curd which exhibit an external orange or light orange color.

7. The plant of claim 3 comprising a plurality of tissues other than a curd which exhibit an external orange or light orange color.

8. The plant of claim 4 comprising a plurality of tissues other than a curd which exhibit an external orange or light orange color.

9. The plant of claim 1 comprising tissues other than a curd wherein the Or gene imparts a predetermined color to the tissues.

10. The plant of claim 2 comprising tissues other than a curd wherein the Or gene imparts a predetermined color to the tissues.

* * * * *